United States Patent
Tompkins et al.

(10) Patent No.: US 9,265,628 B2
(45) Date of Patent: Feb. 23, 2016

(54) PROSTHETIC DEVICE AND CONNECTING SYSTEM USING A VACUUM

(75) Inventors: Michael E. Tompkins, Jamestown, NC (US); Dale Berry, Bloomington, MN (US)

(73) Assignee: Hanger, Inc., Austin, TX (US)

( * ) Notice: Subject to any disclaimer, the term of this patent is extended or adjusted under 35 U.S.C. 154(b) by 1018 days.

(21) Appl. No.: 12/518,074

(22) PCT Filed: Dec. 7, 2007

(86) PCT No.: PCT/US2007/025036
§ 371 (c)(1),
(2), (4) Date: Feb. 1, 2011

(87) PCT Pub. No.: WO2008/073286
PCT Pub. Date: Jun. 19, 2008

(65) Prior Publication Data
US 2011/0125291 A1  May 26, 2011

Related U.S. Application Data

(60) Provisional application No. 60/869,244, filed on Dec. 8, 2006.

(51) Int. Cl.
*A61F 2/78* (2006.01)
*A61F 2/68* (2006.01)
(Continued)

(52) U.S. Cl.
CPC ... *A61F 2/78* (2013.01); *A61F 2/68* (2013.01); *A61F 2002/701* (2013.01);
(Continued)

(58) Field of Classification Search
CPC ....... A61F 2/80; A61F 2/68; A61F 2002/802; A61F 2002/742
USPC .......................................... 623/34
See application file for complete search history.

(56) References Cited

U.S. PATENT DOCUMENTS 5,716,355 A   2/1998  Jackson et al.
5,840,047 A   11/1998 Stedham
(Continued)

FOREIGN PATENT DOCUMENTS

CA     2611492      12/2006
JP     05-337146    12/1993
(Continued)

OTHER PUBLICATIONS

PCT Notification of Transmittal of the International Search Report . . . , International Search Report and PCT Written Opinion from corresponding PCT Application No. PCT/US2007/025036 (6 pages).

(Continued)

*Primary Examiner* — Bruce E Snow
*Assistant Examiner* — Melissa Hoban
(74) *Attorney, Agent, or Firm* — Foley & Lardner LLP

(57) ABSTRACT

The disclosed prosthetic device may comprise a receptacle for receiving a limb of a person; a vacuum pump in fluid communication with the receptacle for maintaining an amount of vacuum used for connecting the receptacle to the limb of the person; a controller; and/or an electronically controllable fluid control device. The controller may be configured to provide a vacuum signature to be displayed at a user interface and/or to control the amount of vacuum used for connecting the receptacle to the limb of the person.

13 Claims, 8 Drawing Sheets

(51) Int. Cl.
 *A61F 2/70* (2006.01)
 *A61F 2/74* (2006.01)
 *A61F 2/76* (2006.01)
 *A61F 2/80* (2006.01)

(52) U.S. Cl.
 CPC .... *A61F 2002/704* (2013.01); *A61F 2002/705* (2013.01); *A61F 2002/707* (2013.01); *A61F 2002/741* (2013.01); *A61F 2002/742* (2013.01); *A61F 2002/747* (2013.01); *A61F 2002/748* (2013.01); *A61F 2002/769* (2013.01); *A61F 2002/7635* (2013.01); *A61F 2002/7655* (2013.01); *A61F 2002/802* (2013.01); *A61F 2250/008* (2013.01)

(56) References Cited

U.S. PATENT DOCUMENTS

| | | | |
|---|---|---|---|
| 2004/0030411 | A1 | 2/2004 | Caspers |
| 2004/0181290 | A1* | 9/2004 | Caspers ........................ 623/34 |
| 2005/0283257 | A1 | 12/2005 | Bisbee, III |
| 2006/0212128 | A1 | 9/2006 | Nachbar |
| 2006/0282175 | A1* | 12/2006 | Haines et al. .................. 623/24 |

FOREIGN PATENT DOCUMENTS

| | | |
|---|---|---|
| JP | 06-020790 U | 3/1994 |
| JP | 08-280707 | 10/1996 |
| JP | 2004-516856 | 6/2004 |
| JP | 2005-034508 | 2/2005 |
| JP | 2005-111141 | 4/2005 |
| JP | 2005-509448 | 4/2005 |
| JP | 2005-527297 | 9/2005 |
| WO | WO 01/70147 | 9/2001 |
| WO | WO 03/099173 | 12/2003 |
| WO | WO 2005/039444 A | 5/2005 |
| WO | WO-2005/105000 | 11/2005 |
| WO | WO 2006/045092 A | 4/2006 |

OTHER PUBLICATIONS

PCT Written Opinion from corresponding PCT Application No. PCT/US2007/025036 (6 pages).
European Office Action for EP Application No. 07853263.7, mail date Oct. 19, 2010, 5 pages.
English translation of Notice of Reasons for Rejection for Japanese Patent Application JP 2009-540305, dated Sep. 12, 2012, 3 pages.
Machine translation of JP 2005-034508, publication date Feb. 10, 2005, 9 pages.
Decision of Rejection and English Translation thereof for Japanese Patent Application No. 2009-540305, dated May 13, 2014, 5 pages.
Office Action for Canadian Patent Application No. 2,672,209, dated Feb. 7, 2014, 3 pages.
Notice of Reasons for Rejection (and its English translation) regarding Japanese Patent Application No. 2009-540305, issued on Sep. 4, 2013, 8 pps.
Canadian Office Action for Application No. 2,672,209, dated Apr. 7, 2015, 3 pages.

* cited by examiner

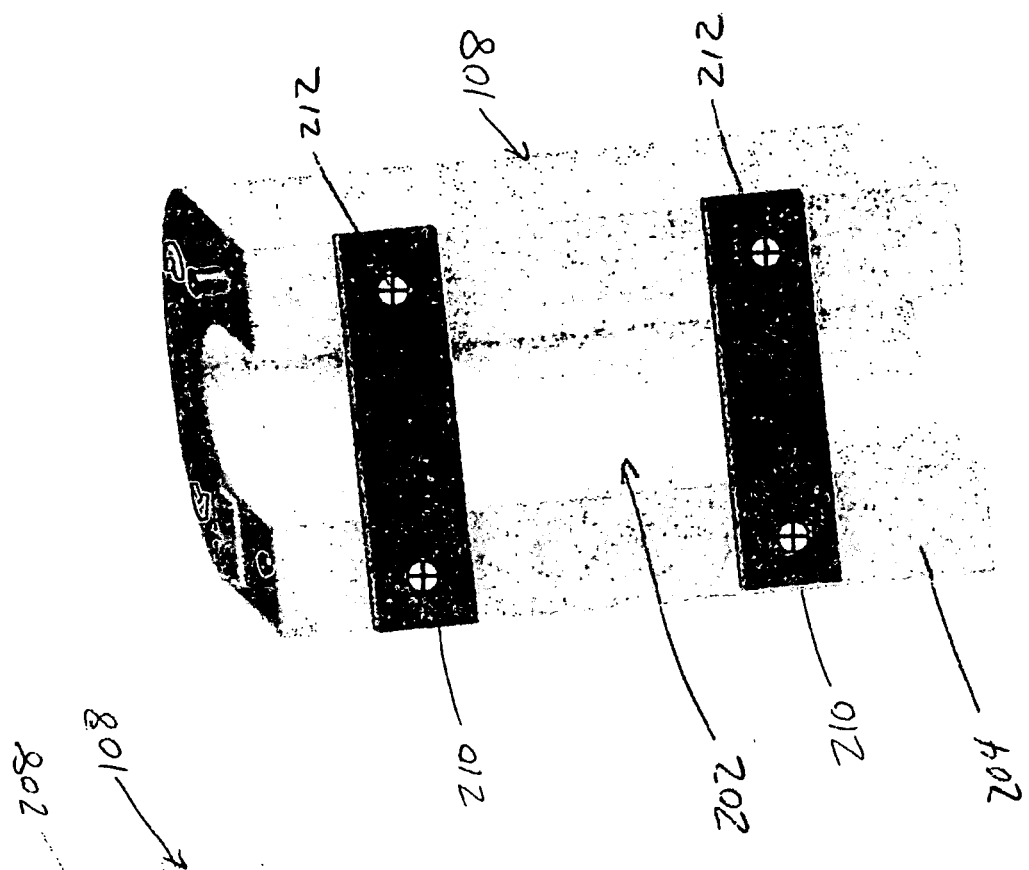
FIG. 2(a)
FIG. 2(b)

PROSTHETIC DEVICE AND CONNECTING SYSTEM USING A VACUUM

CROSS REFERENCE TO RELATED APPLICATIONS

This application is a national stage application of PCT/US2007/025036, filed Dec. 7, 2007, which claims priority from U.S. Provisional Patent Application Ser. No. 60/869,244, filed Dec. 8, 2006, both of which are hereby incorporated by reference herein in their entirety.

BACKGROUND

The present invention relates to prosthetic devices and technology for connecting prosthetic and other devices onto body parts.

In the field of prosthetics, various means are used to connect an artificial limb to a residual limb of a patient, such as an amputee. One such means is to provide an artificial limb having a socket into which the patient's residual limb is inserted and to create a vacuum in the socket to maintain the artificial limb on the residual limb.

A known device uses a manual vacuum pump to create the vacuum used to maintain an artificial limb on a residual leg. In this known device, ambulation causes the manual vacuum pump to actuate under the influence of the patient's body weight and create the vacuum in the socket. Unfortunately, the device is bulky, heavy, and difficult to apply to patients who are lightweight or slight of build. Also, when the patient is sitting, the pump does not function; thus resulting in a loss of vacuum.

Another known device uses an electronic vacuum pump that is operated by batteries to create a vacuum for the connection of an artificial limb to a residual leg. This device, however, is very large, noisy, difficult to adjust with accuracy, and expensive.

These and other known devices have additional drawbacks. For example, they are not well suited to address individual needs of patients or to address changes in a patient's environment. They also are not capable of recognizing and addressing certain situations and/or problems.

SUMMARY OF THE INVENTION

According to one embodiment of the present invention, a prosthetic device may comprise a connecting portion for connecting to a person using vacuum, a control structure for controlling an amount of vacuum used to connect the connecting portion to the person, and an output device for outputting data related to the vacuum for display at a user interface.

According to another embodiment of the present invention, a method for connecting a prosthetic device to a person may comprise connecting a connecting portion of the prosthetic device to the person using vacuum, controlling an amount of vacuum used to connect the connecting portion to the person, and outputting data related to the vacuum for display at a user interface.

According to another embodiment of the present invention, a prosthetic device may comprise a connecting portion for connecting to a person using vacuum, and a control structure for controlling an amount of vacuum used to connect the connecting portion to the person and evaluating data related to the vacuum to control the amount of vacuum based on at least one of fit, function, and status of the prosthetic device and activity of the person.

According to another embodiment of the present invention, a prosthetic device may comprise a connecting portion for connecting to a person using vacuum, and a control structure for controlling an amount of vacuum used to connect the connecting portion to the person, wherein the control structure is configured to receive input from the person to permit control along a substantially continuous spectrum of vacuum adjustment.

According to another embodiment of the present invention, a prosthetic device may comprise a connecting portion for connecting to a person using vacuum and a control structure for controlling an amount of vacuum used to connect the connecting portion to the person. The control structure can include a vacuum pump in fluid communication with the connecting portion for controlling an amount of vacuum used to connect the connecting portion to the person, a vacuum sensing mechanism for measuring the amount of vacuum, an electronically controllable fluid control device for controlling the amount of vacuum used to connect the connecting portion to the person, a controller configured to receive input from the vacuum sensing mechanism and to control the vacuum pump and electronically controllable fluid control device to control the amount of vacuum.

According to another embodiment of the present invention, a prosthetic device may comprise a connecting portion for connecting to a person using vacuum, a pylon connected to the connecting portion, a housing connected to the pylon, and a control structure for controlling an amount of vacuum used to connect the connecting portion to the person. The control structure can include a vacuum pump in fluid communication with the connecting portion for controlling an amount of vacuum used to connect the connecting portion to the person, a vacuum sensing mechanism for measuring the amount of vacuum, an electronically controllable fluid control device for controlling the amount of vacuum used to connect the connecting portion to the person, a controller configured to receive input from the vacuum sensing mechanism and to control the vacuum pump and electronically controllable fluid control device to control the amount of vacuum. The prosthetic device also can include a housing for at least a portion of the control structure, wherein the housing is located on the pylon.

According to another embodiment of the present invention, a prosthetic device may comprise a connecting portion for connecting to a person using vacuum, a control structure for controlling an amount of vacuum used to connect the connecting portion to the person, and at least one of a wireless transmitter for sending information related to the vacuum and a wireless receiver for receiving information related to the vacuum.

According to another embodiment of the present invention, a prosthetic device may comprise a connecting portion for connecting to a person using vacuum, and a control structure for controlling an amount of vacuum used to connect the connecting portion to the person. The control structure can include a vacuum pump in fluid communication with the connecting portion for controlling an amount of vacuum used to connect the connecting portion to the person, a vacuum sensing mechanism for measuring the amount of vacuum in the connecting portion, a pressure sensing mechanism for sensing ambient pressure external to the connecting portion, and a controller configured to receive input from the vacuum sensing mechanism and the pressure sensing mechanism to control the vacuum pump to control the amount of vacuum.

It is to be understood that both the foregoing general description and the following detailed descriptions are exemplary and explanatory only.

BRIEF DESCRIPTION OF THE DRAWINGS

These and other features, aspects and advantages of the present invention will become apparent from the following description and the accompanying exemplary embodiments shown in the drawings, which are briefly described below.

FIGS. 2(a) and 2(b) are perspective and bottom views, respectively, of a housing of the control structure shown in FIG. 1.

DETAILED DESCRIPTION OF THE INVENTION

A prosthetic device and connecting system according to a preferred embodiment of the present invention will be described in detail below with reference to FIGS. 1-6. Though the preferred embodiment is described in the context of an artificial leg, it is contemplated that the invention could be used in other contexts in which a device is connected to a patient's body. For example, the device could be an artificial arm, an orthotic component, or other past, current, or future orthotic products that use vacuum or similar methods to connect the orthosis to the patient. The connection method need not be a fully encompassing socket like a prosthesis. The vacuum could assist the connection device or may be used as a stabilizer in connection with some other connection methods.

Figure 1:
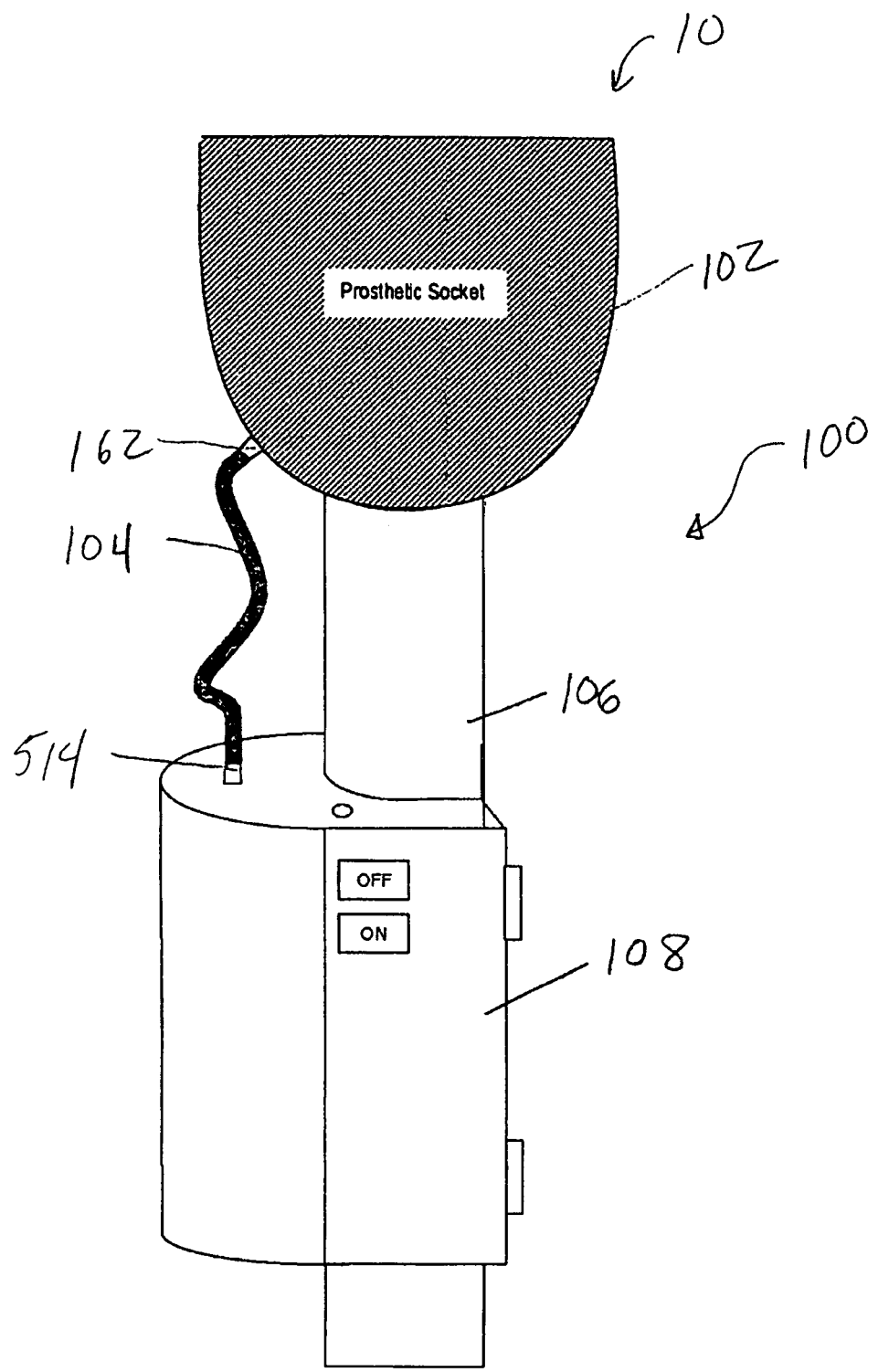
FIG. 1 is a side view of a portion of a prosthetic device having a control structure for connecting the prosthetic device to the residual limb of a person or patient, according to an embodiment of the present invention.

FIG. 1 shows a portion of a prosthetic device 10 according to this embodiment of the present invention. The prosthetic device 10 can include, among other things, a connecting portion 102 for connecting to a person using vacuum, a pylon 106, an artificial foot 154, and a control structure 100 for controlling an amount of vacuum used to connect the connecting portion 102 to the patient.

Figure 5:
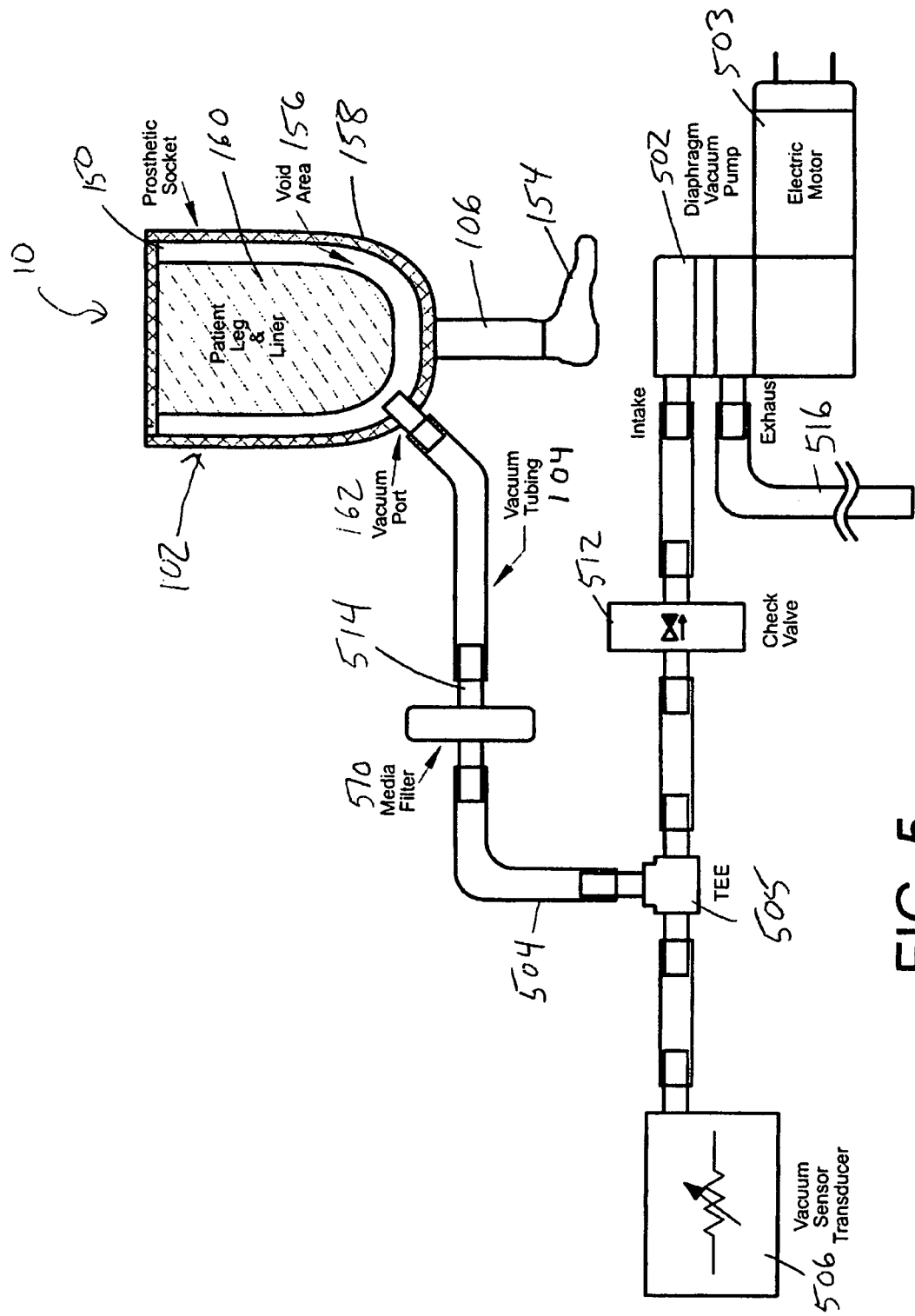
FIG. 5 is schematic diagram showing the components of the vacuum system inside the housing of the control structure shown in FIG. 1.

The connecting portion 102 can be a receptacle (such as a prosthetic socket) for receiving a limb of a patient and can be any configuration suitable for maintaining a vacuum, including those known in the art. As seen in FIG. 5, for example, the socket 102 can comprise an inner liner 160, an outer casing 158, and a sealing mechanism (not shown). Preferably, the socket design and fabrication techniques will adhere to specific socket design criteria to ensure total contact of the residual limb to ensure there are no voids between the socket, liner and the residual limb. More preferably, the socket can be cast and designed utilizing one of the following existing art socket variations: (1) Total Surface Bearing (TSB) socket as taught at UCLA commencing 1985; (2) the Hanger Comfort-Flex Trans Tibial socket design as taught at the Hanger Education facility in Oklahoma City commencing 1994; (3) ICEROSS silicone Socket technique as described by O. Kristinsson at the 1984 National American Orthotic and Prosthetic Association assembly; and (4) 3S (Silicon Suction Socket) technique as described in the *Journal Of Prosthetics & Orthotics, Evolution and Development of Silicon Suction Sockets for the Below Knee Prosthesis,* 1989, Volume 1, Num 2, Pages 92-103 (which is hereby incorporated by reference in its entirety).

The inner line 160 can be configured to fit onto the patient's residual limb and into the outer casing 158. The inner liner can be formed of conventional liner materials. Preferably, the residual limb will be fit with a total contact silicone type or comparable liner that has a cloth or similar outer covering. There are numerous variations of liners from numerous manufactures that will accommodate the function and proper application of this device. The liner must be properly fit to the patient and contain an outer cloth or similar covering to provide appropriate and necessary wicking and movement between the silicone liner and the outer prosthetic socket. Examples of an appropriate liner would be the Alpha Liner by Ohio Willow Wood, the Alps liner or Ossur IceRoss Liner.

The outer casing 158 can be configured to have a volume and shape that will receive a substantial portion of the patient's residual limb (or other appendage or part of the patient, as appropriate). The outer casing 158 has an opening 150 through which the residual limb 152 with the connected inner liner 160 can be inserted into the outer casing 158, such that they will be disposed in a space within the outer casing 158. The outer casing 158 can be formed of conventional materials.

The sealing mechanism can be configured to form an airtight seal between the patient's residual limb and the socket 102. For example, the sealing mechanism can be a non-foamed, nonporous polyurethane suspension sleeve which rolls over and covers the socket 102 and a portion of the residual limb. There are numerous existing and available products on the market that will serve as the sealing mechanism. The inner surface of the suspension sleeve preferably is designed with a material that will provide a seal against the skin on the patient's thigh and the outer surface of the prosthetic socket to provide an airtight seal for the vacuum. Examples of an appropriate suspension sleeve include, but are not limited to, the Cinch Sleeve by DAW, Durasleeve, Gel Suspension sleeve by IPOS or the Alps line of suspension sleeves. After the silicone liner is fit properly to the residual limb, the silicone liner and residual limb are then placed into the prosthetic socket. The suspension sleeve then can be applied over the outer surface of the prosthetic socket and rolled up onto the thigh portion of the residual limb. This suspension sleeve can provide the vacuum seal within the prosthetic socket to enable the device to achieve appropriate vacuum (measured in inches of mercury) and prosthetic suspension.

When the patient's residual limb is inserted into the socket 102, a void area 156 will be formed between the outer casing 158 and the inner liner 160. A vacuum port 162 can be provided in the outer casing 158 to permit fluid communication (typically gas or air) between the void area 156 and the control structure 100, such that a vacuum can be created and maintained in the void area 156. This vacuum can be strong enough to create an adhesive force so that the socket 102 can be securely connected to the residual limb.

The socket 102 can be mounted on and connected to an end of the pylon 106, as shown in FIG. 5 using existing, available, or future products and technology. The other end of the pylon 106 can be connected to the artificial foot 154 or another suitable base so as to allow the patient to stand and walk. In one example, the pylon can be a 30 mm diameter cylinder connected to the socket and artificial foot using conventional methods. However, it should be recognized that any shape or configuration of pylon can be used, such as rectangular or other suitable shape or configuration.

The control structure 100 can include a housing 108 that can be configured to contain structure (described in more detail below) for creating, monitoring, and maintaining a vacuum in the void area 156 in socket 102. The housing 108 can be, for example, connected to the pylon 106 and connected to the vacuum port 162 of the socket 102 by a vacuum line 104. The housing 108 preferably provides and monitors the vacuum supplied to the prosthetic socket 102 via the vacuum line 104.

The housing 108 can be any suitable material, such as a metal or plastic, and can be formed in any suitable shape. Preferably, the housing 108 is an essentially rectangular box with highly radiused sides, as seen in FIGS. 2(a) and 2(b) or a cylindrical box as seen in FIG. 1. As seen in FIGS. 2(a) and 2(b), the housing 108 can have a semi-circular cutout 202 on its back 204 running vertically along its entire length such that it is partially wrapped around the pylon. The cutout 202 allows the housing 108 to be disposed around the pylon 106 rather than being connected in front of the pylon 106. The arrangement of the housing 108 with the cutout 202 works better with a cosmetic cover (not shown) placed over the pylon because the housing as a whole will extend out less from the pylon, and the radiused corners 208 of the housing can match the curvature of a leg. The arrangement of FIGS. 2(a) and 2(b) can be particularly advantageous because control structures that mount in front of the pylon create difficulties in fabricating the cosmetic cover and can make unsightly bumps in an otherwise smooth cover. Of course, it should be recognized that the cutout 202 can be any suitable shape that matches the shape of the pylon.

The housing 108 can be connected to the pylon 106 using upper and lower connection straps 210. Each connection strap is secured to the housing 108 on either side of the cutout 202 through the use of fasteners 212, such as bolts, a hook and loop system, or any other fasteners known in the art. The connections straps can be adjustable so that the housing can be fixedly secured to the pylon 106.

Figure 3:
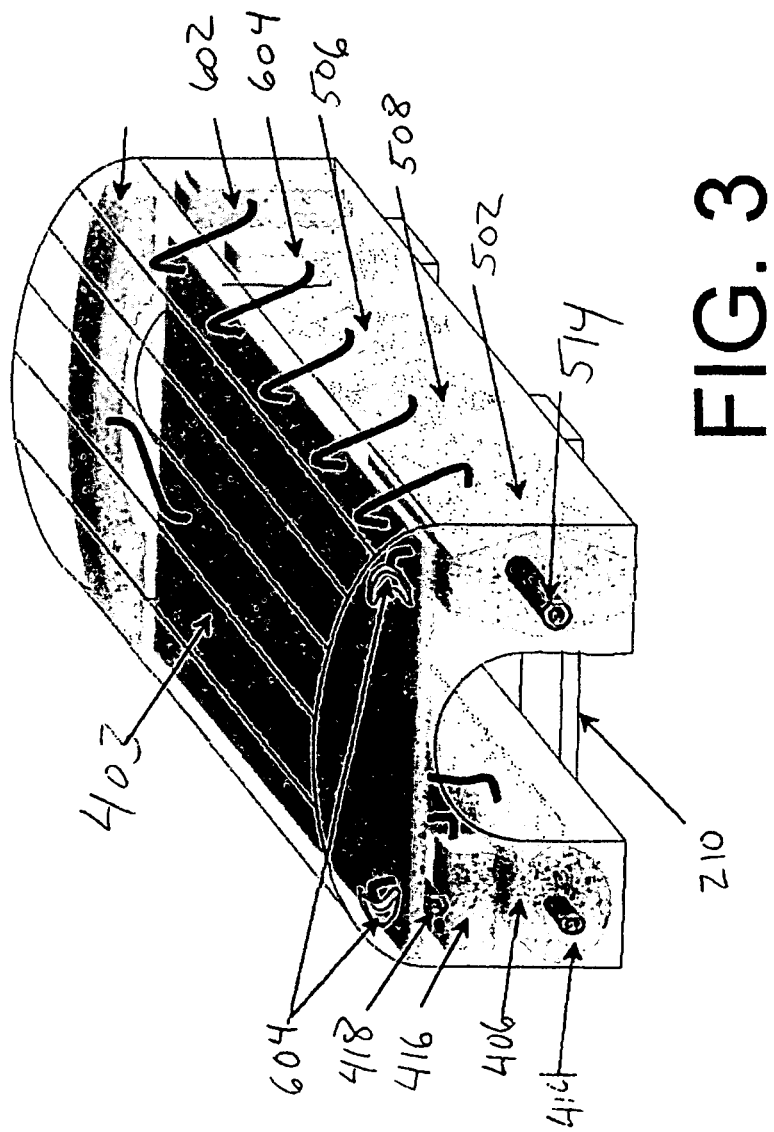
FIG. 3 is a schematic view of components of electronic and vacuum systems inside the housing of the control structure shown in FIG. 1.
Figure 4:
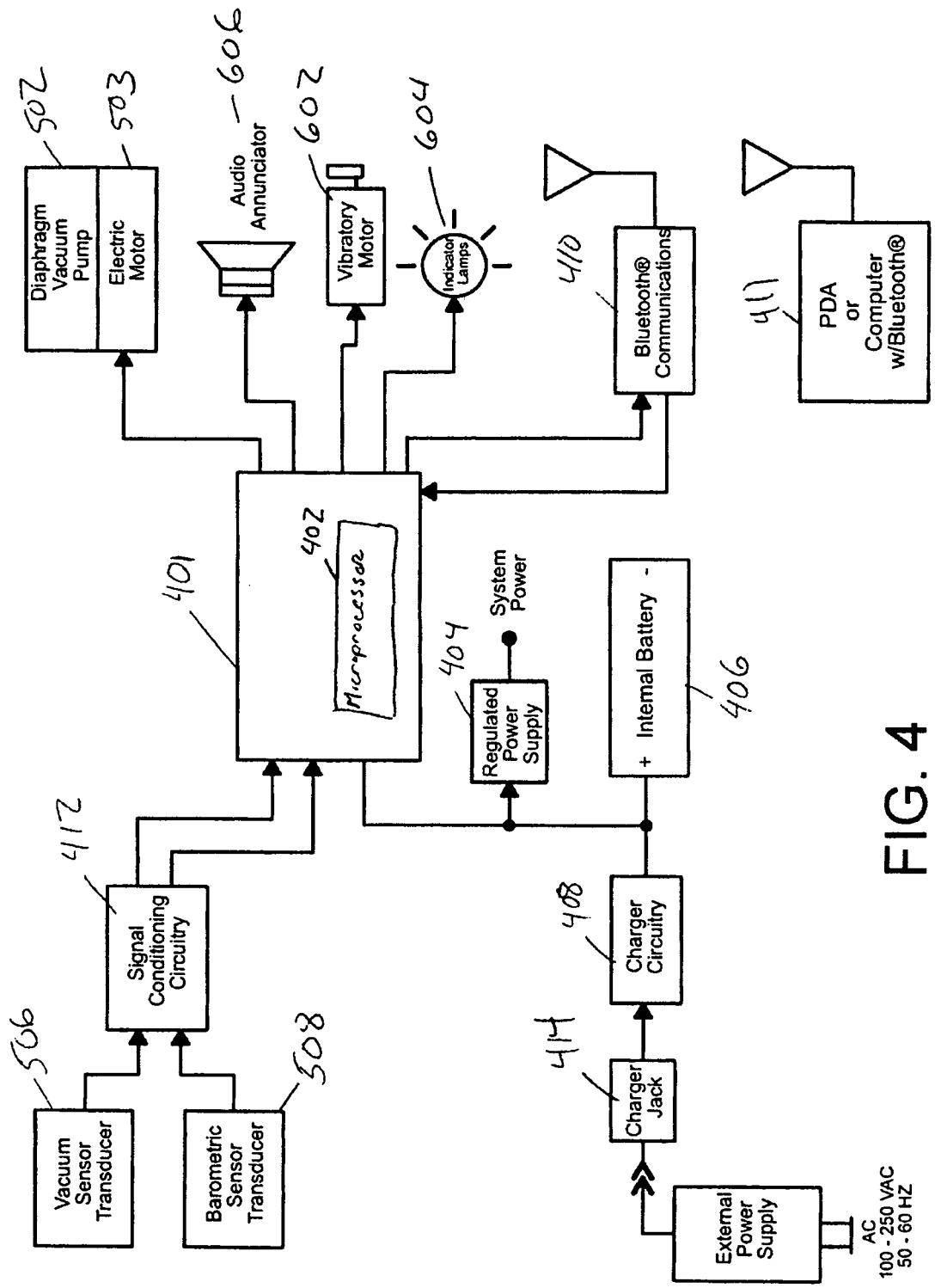
FIG. 4 is a circuit diagram showing the components of the electronic system inside the housing of the control structure shown in FIG. 1.

The housing 108 houses the electronic and vacuum system components of the control structure, as depicted in FIGS. 3-5. The electronic and vacuum systems work in cooperation to create a vacuum for the socket 102 so as to maintain the prosthetic device 10 on the residual limb or other appendage.

Different switches can be used to turn the systems of the control structure on or off. For example, a simple ON/Off Rocker switch 416 can be mounted on the housing 108. Alternatively or additionally, a remote ON/OFF port 418 can be mounted on the housing 108. The remote ON/OFF port can be connected to a power ON/OFF switch that is remotely mounted, for example on the cosmetic cover that covers the socket 102 and the pylon 106. The remote ON/OFF switch can make it simpler and easier to find the switch, especially in the case of thick or dense cosmetic covers.

The electronic system is shown in FIGS. 3 and 4 and preferably includes a controller comprising control circuitry 401, one or more internal batteries 406, a regulated power supply 404, charger circuitry 408, a wireless transceiver 410, and signal conditioning circuitry 412.

The control circuitry 401 can be mounted on a circuit board 403. The control circuitry 401 can include a microprocessor 402 having a permanent memory for storing software for the operation and monitoring of the electronic and vacuum systems and a reprogrammable memory for storing patient data and system variables. The software can comprise the procedures, algorithms and all other operation parameters and protocols for the control structure's individual components. For example, the analog signals from the vacuum sensor 506 and the barometric sensor 508 that are amplified and filtered by the signal conditioning circuitry 412 will be converted to digital values and stored in memory. These digital values can then be used by various aspects of the software to determine when to activate the motor 503 for the vacuum pump 502, the vibration motor 602, the visual indicators 604, and the audio annunciator 606. For example, almost any microprocessor could execute the algorithms, and the software language could be assembly code, C, C#, BASIC, or the like. A preferred microprocessor 402 is MSP430F1611 manufactured by Texas Instruments, Inc. (although MSP430F169 also could be used). The microprocessor could form part of a microcomputer having the input and output (I/O) components plus the permanent reprogrammable and random access memory, embedded in a single device.

The microprocessor 402 may also contain or be connected to a real-time clock and calendar device, also referred to in the industry as RTC, (not shown) to provide a time and date stamp for events (examples of which are described below) that are stored in a system log. A preferred RTC device is M41T80 manufactured by ST Microelectronics. The RTC can have an auxiliary power source to allow the RTC to continue operating even if the main battery 406 is shutoff or completely discharged. This power source could be a device known in the industry, such as a SuperCap capacitor or a miniature lithium or silver oxide cell, like those used in a hearing aid.

The internal battery or batteries 406 can power the electronic and vacuum systems. Preferably the batteries 406 will enable a minimum of 24 hours of constant use to ensure a full day of activity and that can be recharged over a short period of time (e.g., two to three hours) so that while the patient rests the control structure can recharge quickly. Each battery 406 can be, for example, a lithium-ion or lithium polymer battery. A presently preferred battery is a 3.7 Volt lithium-ion cylindrical cell in a package that is 18 mm in diameter and 50 millimeters in length. It has a capacity of 1500 milliampere-hours. One version of this cell is known as CGR18500 and is available from multiple manufacturers, including Panasonic Industrial Battery Co. The battery placement could be an internally mounted type or an external user replaceable type. The preferred method is internal mounting which allows direct control and protection of the battery and eliminates issues with environmental problems and customer abuse.

The regulated power supply 404 receives power supplied by the battery or batteries 406 and can supply power to the various system components, such as the microprocessor 402, the electric motor 502, the vibration motor 602, and other components that require power. The normal battery operating range is 2.75 volts to 4.2 volts. The regulated power supply circuitry can be used to convert this varying battery voltage into two different regulated voltages. A 3.3 volt output preferably is used to power the electronic components and a 6.8 volt output preferably is used to power the vacuum pump motor and the solenoid valve (if used). A SEPIC (Single Ended Primary Inductance Converter) regulator topology can be used for the 3.3 volt supply. This unique type of regulator provides a constant voltage output whether the battery voltage is higher or lower than the 3.3 output. The main component in this regulator is a Linear Technology LT 1615. A boost regulator topology can be used to create the 6.8 volt supply. This output is always higher than the battery range so this regulator boosts (increases) the voltage up to 6.8 volts. The reason this power supply is rated at 6.8 volts while the vacuum pump motor and solenoid valve (if used) are rated at 6 volts, is to compensate for the internal losses in the motor driver, other circuitry and wiring. Therefore the power that reaches the pump motor and solenoid valve (if used) will always be 6.0 volts or greater and the pump will operate at its expected parameters. The main component in this boost regulator circuit is the Linear Technology LT1935.

The microprocessor 402 can be configured, by means known in the art, to monitor the status of available power from the internal battery 406 and the regulated power supply 404 and issue a warning to the patient if the available power is below a predetermined threshold. For example, if the battery voltage reaches a warning level (e.g., 3.0 volts), the system will annunciate the condition to the patient so as to tell the patient that the battery and power systems have some minimal operational time (e.g., one hour) and should be re-charged soon. This annunciation, for example an audio annunciation using the audio annunciator 606, can occur in short bursts (e.g., every five minutes) until the system reaches the critical point of shutdown, or until the battery is re-charged. As another example, the annunciation could be in the form of a vibration of the device using a vibratory motor 602 providing short vibrations every 5 minutes until the system reaches the critical point of shutdown, or until the battery is re-charged. As another example, the annunciation could be in the form of three successive cycles of one second of vibration followed by one second of non-vibration. This would occur every five minutes until the system goes into low voltage shutdown, or until the battery re-charge is initiated.

The charger circuitry 408 can be provided for charging and cell protection of the battery 406. Presently preferred charger circuitry 408 is based on a BQ24103 integrated circuit manufactured by Texas Instruments. The lithium-ion battery cell is protected from over-voltage, over-charge, under-voltage, and over-discharge by a circuit that is based on the UCC3952 integrated circuit manufactured by Texas Instruments. The charger circuitry 408 can be connected to a port or charger jack 414 on the housing 108. This port 414 would allow the patient to charge the power system from the ankle or foot area using an external power supply, such as a conventional AC power source with a voltage of 100-250 VAC at 50-60 Hz. The port 414 can provide the advantages of avoiding the need to provide access holes on the cosmetic cover that goes over the pylon 106 and socket 102 and avoiding the need to have the patient remove the cosmetic cover to charge the battery or power system.

The wireless transceiver 410 can be, for example, a Bluetooth® radio for wireless telemetry. The transceiver 410 exchanges signals with the microprocessor 402 so that the operational values of the electronic and vacuum systems can be monitored and adjusted by a remote station or transmitting/receiving device 411 while the prosthetic device is on the patient. A presently preferred wireless transceiver 410 is based on KC22 Bluetooth radio manufactured by KC Wirefree, Inc.

The remote station or transmitting/receiving device 411 can send signals to and receive signals from the wireless transceiver 410 to monitor parameters of the control structure and provide input to change parameters or controls using a graphical user interface, as described in more detail below. The remote station 411 can be a laptop computer, a computer workstation, handheld PDA, or the like. A presently preferred remote station 411 is IPAQ 2495B Personal Digital Assistant (PDA) manufactured by Hewlett Packard. The transmission between the wireless transceiver 410 and the remote station 411 can involve technology other than Bluetooth® radio, such as infrared waves, microwaves, radio waves, and other forms of electromagnetic radiation transmission. Additionally, a direct wired method could connect the device to the PDA or computer.

The vacuum system is shown in FIGS. 3, 4, and 5. The vacuum system can be connected to the socket 102 via the vacuum tube 104. The vacuum tube 104 is connected to the vacuum port 162 on the socket 102 and to a vacuum line intake port 514 on the housing 108.

The vacuum system preferably includes a vacuum pump 502, an electric motor 503, vacuum tube 504, various component interconnections using a vacuum sensing mechanism or sensor 506, a barometric sensor 508, a media filter 510, and a check valve or solenoid 512. Within the housing 108, preferably the vacuum line intake port 514 connects to the vapor trap/filter or a media filter 510. The media filter can be external to the case for easy replacement by the patient/practitioner. The other side of the vapor trap/filter 510 connects to a vacuum tube 504 which leads to a tee 505. One side of the tee 505 is connected to the intake side of the vacuum pump 502 via the check valve 512. The other side of the tee 505 is connected to a vacuum sensor 506.

The vacuum pump 502 may be a diaphragm pump driven by a DC motor 503. A suitable vacuum pump is available from many manufacturers. A presently preferred combined vacuum pump 502 and motor 503 is a model number VMP1625MX-06-110-NC manufactured by Virtual Industries, Inc. A conventional motor driver (not shown) can be used as the interface between the microprocessor 402 and the vacuum pump 502 and the DC motor 503. The motor drive can be used to vary the speed of the motor 503 using pulse width modulation techniques. A presently preferred motor driver circuitry is based on the SI9986 H Bridge Driver manufactured by Vishay Semiconductor Co. The intake side of the pump 502 creates the suction that keeps the prosthetic device on the residual limb. The exhaust side of the vacuum pump connects to vacuum tubing 516, which is routed to the distal end of the prosthesis. This exhaust tubing 516 allows any moisture to drain and acts as a muffler for the vacuum pump 502.

The vacuum sensing mechanism or sensor 506 is an electronic device that converts vacuum or pressure within the socket 102 to a millivolt differential voltage for the purpose of measuring the amount of vacuum within the receptacle or socket. The vacuum sensor 506 could be selected from any suitable type of sensors known in the art, but a presently preferred vacuum sensor 506 is a 24PC15SMT manufactured by Honeywell Corporation. The differential signal is amplified and scaled via the signal conditioning circuitry 412, which contains amplifying and scaling components, as is known in the art. After amplification and scaling, the differential voltage is then presented to the Analog to Digital (A/D) converter in the microprocessor 402 for converting the varying vacuum analog signal to a digital number representing the vacuum value.

Similarly, as seen in FIG. 4, the barometric sensor (or atmospheric sensor or a pressure sensing mechanism for sensing ambient pressure) 508 is also an electronic device that converts the current absolute barometric pressure outside the prosthetic device to a millivolt differential voltage. The barometric sensor 508 could be selected from any suitable type of sensors known in the art, but a presently preferred barometric sensor 508 is 26PCDFFA6A manufactured by Honeywell Corporation. The differential signal is amplified and scaled via the signal conditioning circuitry 412. After amplification and scaling, the differential voltage is then presented to the Analog to Digital (A/D) converter in the microprocessor 402. The microprocessor 402 can continuously monitor the atmospheric pressure using the barometric sensor 508 and use this information to offset and calibrate the vacuum sensor 506 to ensure the vacuum in the socket is correct for the environment. That is, the barometric sensor 508 can be used as a reference sensor for calibrating the vacuum sensor and compensate for barometric or altitude changes. Thus, the vacuum control parameters can be adjusted to provide the same suction and feel to the socket at various barometric or altitude changes. For example, a control structure calibrated at sea level can work exactly the same at 5000 ft above sea level.

The vapor trap/filter or a media filter 510 is provided to ensure the cleanliness of the vacuum system. A presently preferred media filter 510 is a model FMH332-3-05-6 filter with a 5 micron screening level manufactured by Beswick Engineering. However a 40 micron (e.g., model FMH332-3-40-6) or 25 micron media filter could also be used.

The check valve 512 is used to ensure that the fluid (typically air or gas) in the vacuum system only flows toward the direction of negative pressure provided by the vacuum pump 502. The check valve only allows fluid to flow through it in one direction, in particular toward the vacuum pump as shown in FIG. 5. A suitable check valve 512 may be model 64100 manufactured by US Plastics Corp.

More preferably, an electronically controllable fluid control device 512, such as an electrically operated solenoid valve 512, may be used instead of a mechanical check valve. A suitable solenoid valve is available from many manufacturers. A preferred solenoid valve 512 is a model is the KSV-2 a 2-way normally closed solenoid valve distributed by Clark Solutions. According to a preferred embodiment, the solenoid valve is of a normally closed version, i.e., when the solenoid is not activated the valve is shut or closed. When the proper voltage is applied to the solenoid, the valve will open and will remain open as long as the solenoid is powered. A conventional motor driver (not shown) can be used as the interface between the microprocessor 402 and the electrically controlled solenoid valve 512. The driver circuit (supplied in the control electronics 401) provides power to the solenoid valve when the program stored in the microprocessor 402 of the controller determines the valve should open. A preferred motor driver circuitry is based on the S19986 H Bridge Driver manufactured by Vishay Semiconductor Co.

The solenoid valve may provide the benefit that the valve can be opened and close at any time as determined by the program in the microcomputer. In contrast, the mechanical check valve operates based on differential pressure and may not open or close completely unless the differential pressure is met. Therefore, the requirement to remove the differential pressure needed to open or close the valve is removed, and the controller, through the control electronics 401, may control the sequence of operation of the pump and valve such that the pump 502 may be operated for a second before the valve 512 is opened. In other words, the controller can take the vacuum to a higher level on the pump side then operate the valve 512. Additionally, an electrically operated solenoid valve 512 provides a positive seal to virtually eliminate valve leakage or reduce it to an acceptable level.

Furthermore, a solenoid valve may allow the vacuum to be vented to the atmosphere to reduce the socket vacuum. For example, if the patient is sitting for a long period of time, the vacuum in the socket could be reduced to make the prosthesis more comfortable. The patient could control this feature through a user interface located on the housing 108 or a remote receiving/transmitting device which transmits, wirelessly or by wire, control signals to the control electronics in the housing. Alternatively, the control electronics may control this feature as an automatic function after analyzing the vacuum signature, as described below. This feature for controlling the reduction in pressure feature could also be beneficial for reducing the vacuum so as to remove the prosthesis. In such an instance, this feature may be activated by the patient.

According to another embodiment of the present invention, the electronically controllable fluid control device 512 may control the amount of vacuum supplied to the receptacle or socket using an orifice whose opening is adjustable from a fully closed state to a fully open state in a continuously opening fashion. In this embodiment, the degree of openness for the valve will depend upon the amount of voltage or current supplied to the control device by the control electronics of the controller. Alternatively or additionally, the fluid control device may be a valve that is controlled by the controller to release at least a portion of vacuum pressure based on user input (i.e., a three-way valve to allow bleed off).

The control structure can include one or more devices used to warn the patient or user that there may be a problem with the control structure. These warning devices may include one or more of the following: a vibration motor 602 for causing the device to vibrate, visual indicators 604, and an audio annunciator 606. Thus, annunciation may be vibratory, visual, and/or auditory. In the case of vibratory annunciation, the small vibration motor 602 drives an offset cam load which creates an unbalanced condition and causes vibration. A motor driver can be used as the interface between the microprocessor 402 and the vibration motor 602. This motor driver can be used to vary the speed of the vibration motor using pulse width modulation techniques. In the case of the visual indicators 604, these devices can take the forms, for example, of light emitting diodes (LEDs), lamps, Liquid Crystal Displays (LCD), or the like. The audio annunciator 606 can be any device capable of creating a sufficient and recognizable audio signal.

Now that the basic structure of the control structure has been outlined, the operation of the device will now be described.

When the power switch is activated using the ON/OFF rocker switch 416 or a remote ON/OFF switch via the ON/OFF port 418, the electronic and vacuum systems will initialize and prepare for operation. The microprocessor 402 will first perform a system check to verify that all critical components are within their respective operational ranges. Any sections or components not performing correctly will initiate an error condition and force the system to annunciate the error via the vibration motor 602, the visual indicators 604, and/or the audio annunciator 606 and shut down.

If all critical components are working correctly, the microprocessor 402 can read the atmospheric reference from the barometric sensor 508 continuously or intermittently and use the reference to calibrate the vacuum sensor 506, if desired, such that barometric or altitude changes are compensated by the controller; thus providing a consistent suction and feel regardless of the external ambient pressure. Next, the system will read the socket vacuum (i.e., the vacuum in the vacuum system and in the void area 156 of the socket 102) using the vacuum sensor 506, and compare the socket vacuum to preset limits.

If the socket vacuum is below the initiation threshold, the microprocessor will turn on the motor 503, which in turn drives the vacuum pump 502, and operate or open the solenoid check valve 512 to start a vacuum cycle. The initiation threshold is the vacuum level below which the microprocessor 402 will initiate operation of the motor 503 to drive the vacuum pump 502 to actively pull the vacuum. The vacuum pump 502 will continue to pull the vacuum until such time that the microprocessor 402 registers that the specific maximum desired vacuum level within the socket has been achieved. For example, the initiation threshold can be set at 12 inches of mercury and the maximum desired vacuum level can be set at 15 inches of mercury. Therefore, when the control structure is turned on, the vacuum pump 502 will be initiated if the vacuum is below 12 inches of mercury and will continue to increase vacuum until 15 inches of mercury is achieved. The microprocessor 402 will then turn off the motor 503 to the vacuum pump 502 and turn off or close the solenoid check valve 512. The microprocessor 402 will continually monitor the vacuum within the socket 102, and once the vacuum within the socket drops to 12 inches of mercury, the vacuum pump 502 (via the motor 503) and solenoid check valve 512 will be automatically initiated to increase the vacuum until 15 inches of mercury is achieved. Of course, it should be recognized that both the initiation threshold and the maximum desired vacuum settings can be any suitable settings, and they also can be adjusted by inputting these values into the microprocessor 402, for example, via the remote station 411 (a remote receiving/transmitting device) and the wireless transceiver 410.

In regard to this adjustability, the controls on the remote station 411 (or wireless monitoring device) may allow adjustment and fine tuning of the operating parameters of the vacuum system. For example, the maximum vacuum level may be adjustable in increments of 0.1 inches of mercury up to the maximum allowable of the system which would normally be around 20 inches of mercury. Also, the initiation threshold vacuum level is adjustable in increments of 0.1 inches of mercury from an arbitrary minimum of 5 inches of mercury up to the maximum vacuum level of 20 inch of mercury.

The level of adjustability is beneficial. A conventional device typically provides a broad vacuum window to prevent the pump from triggering too easily (i.e., every time the initiation threshold is crossed). Even in normal operation the vacuum in the socket can vary by a considerable amount (e.g., by 3 to 4 inches of mercury). Consequently, the built-in initiation threshold in conventional devices may be set well below the maximum set vacuum level (e.g., 5 to 7 inches of mercury below the maximum set vacuum level) to reduce the likelihood that the initiation threshold will be crossed during normal operation. Otherwise, the pump might trigger almost on every step. However, the problem is that some patients can feel a 5 to 7 inch of mercury change in the vacuum of the socket. Thus, the 5 to 7 inch of mercury range is too broad and at the lower end the socket feels loose or spongy. Even if a running average is calculated to reduce this effect, it will only work correctly under certain dynamic conditions (such as at a slow walk).

For example, FIG. 6(*a*) shows a normal vacuum signature, which is a series of sequential data points from vacuum measurements taken by the vacuum sensing mechanism 506. If the initiation threshold was set at 16 inches of mercury and there were no step-by-step averaging calculations, the pump would operate every step. To compensate, the vacuum is taken to a higher level to limit the excursions or variations so that, on heel strike, the initiation threshold is not crossed but now the patient is operating at a higher vacuum level that may not be comfortable.

According to one embodiment, the system monitors every step and makes various calculations about the vacuum level. One embodiment compares the average vacuum level to the initiation threshold to trigger the pump, not the vacuum level at each step. With such averaging schemes the initiation threshold can be set to a minimum or one to two inches of mercury below the maximum level. Thus, allowing a comfortable yet strong lower vacuum level for the patient to be set and tight control to be maintained while still eliminating excessive pump cycling.

Upon initiation of a vacuum cycle, the microprocessor 402 will activate a timer. If the initiation threshold is not achieved within this first time limit, an error condition will occur where the vacuum pump 502 and its motor 503 will stop and the error will be annunciated using the vibration motor 602, the visual indicators 602, and/or the audio annunciator 606. A presently preferred first time limit is one minute. This action, the time required to perform the action, and the conclusion state can be stored in the microcomputer memory (i.e., the system log) for future reference.

If the vacuum reaches the initiation threshold within the first time limit, the microprocessor will start another timer and allow the vacuum pump 502 to continue running until the maximum desired vacuum level is achieved. If the maximum desired vacuum level is not achieved within this second time limit, an error condition will occur, the vacuum pump 502 and its motor 503 will stop, and the error will be annunciated using the vibration motor 602, the visual indicators 602, and/or the audio annunciator 606. A presently preferred second time limit is thirty seconds. This action, the time required to perform the action, and the conclusion state are stored in the microcomputer memory, or the system log, for future reference.

If the maximum desired vacuum level is achieved within the second time limit, the vacuum pump 502 and its motor 503 will be shut off. The microprocessor will then continue to monitor the socket vacuum. If the socket vacuum drops to the level of the initiation threshold, the vacuum pump 502 and its motor 503 and the timer will start again to attain the maximum desired vacuum level.

The microprocessor 402 can be utilized to detect small leaks and correct the vacuum before the initiation threshold is reached. For example, the vacuum level can be monitored by the program and embedded algorithms to differentiate between modes of operations, such as static (sitting or standing still), dynamic (walking), and transitional. Preferably the system repeatedly updates the mode of operation (for example, every two seconds). Other system calculations and determinations can account for the mode of current operation.

The static mode can be detected by identifying certain expected characteristic(s) of the vacuum signal. For example, if the vacuum signal is within its normal range, i.e., higher than the initiation threshold and less than the maximum, and is not changing more than an insignificant amount (e.g., 0.2 inches of mercury) either up or down compared to the average vacuum level over a predetermined period (e.g., 2 seconds), it will be determined that the patient is in a static condition. The average value will be continually updated to allow for subtle patient movements that could occur while sitting or standing still.

The dynamic mode can be detected by identifying other expected characteristics of the vacuum signal. For example, if the vacuum signal is within the normal range as described above, the signal is increasing and then decreasing but still remaining substantially near the average value, the patient will be determined to be in a dynamic mode. More specifically, if the vacuum signal is moving from a higher than average level to a lower than average level and then back to the higher than average level, and basically remains around an average value, the system will be considered to be in a dynamic mode. For example, if the average vacuum signal is 15 inches of mercury and the vacuum signal starts moving from 14.5 to 15.5 inches of mercury and continues this pattern while occurring at least once every two seconds, the system will be considered to be in a dynamic mode. A moving average could be constantly updated to compensate for various changes in walking speed or pattern.

A series of convoluted vacuum signal movements that still remain within the minimum to maximum zone could suggest that the patient is in a transitional mode, such as moving from sitting to standing. This information may or may not be stored in the system log as a transition.

If it is determined that the patient is in static mode, the system can be used to evaluate whether there is a slow leak. Every predetermined time period (for example, one minute) a new average value will be calculated based on multiple measurements (preferably 100 to 500 per second) taken during that time period. This new average value will be placed into a FIFO (First In First Out) buffer, which stores the average value determinations for, for example, the last ten time periods. This new average value will be compared in some manner to the previous ten average value determinations. For example, the new average value could be compared to an average of the previous ten average value determinations or some other mathematical comparison. If a continuous rate of change of the average value determination is dropping more than a predetermined change value (for example, 0.1 inches of mercury per minute), a slow leak condition is detected and recorded. At this point it is anticipated that the condition will continue, and the pump will be activated and the vacuum will be restored to the maximum level. The predetermined change value can be altered via the graphic user interface to accommodate variations in the prosthetic or orthotic device and their respective components. Therefore the system can respond to minor variations in vacuum loss before the initiation threshold is reached.

If it is determined that the patient is in dynamic mode, the system also can be used to evaluate whether there is a slow leak, but it accounts for expected changes caused by the dynamic mode. If the wearer is in a dynamic mode (walking) the system will calculate an average vacuum value for each step based on multiple measurements (preferably 100 to 500 per second) taken during that step. This will establish an average comparison value for future measurements. The new average value for each step will be placed into a FIFO (First In First Out) buffer, which stores the average value determinations for, for example, the last ten steps. This new average value will be compared in some manner to the previous ten average value determinations. For example, the new average value could be compared to an average of the previous ten average value determinations or some other mathematical comparison. If a continuous rate of change of the average signal is dropping more than a predetermined change value (for example, 0.2 inches of mercury per step), a dynamic leak condition is detected and recorded. At this point it is anticipated that the condition will continue, and the pump will be activated and the vacuum will be restored to the maximum level. This information allows for a determination of whether the vacuum leak is happening while the patient is walking. The predetermined change value can be altered via the graphic user interface to accommodate variations in the prosthetic or orthotic device and their respective components.

The pump also can be activated quickly under extreme conditions, in either the static or dynamic mode. For example, it can be immediately activated if the initiation threshold is reached or if an extreme rate of change is detected. An extreme rate of change can be detected, for example, by calculating an average vacuum value for each predetermined time period or each step based on multiple measurements (preferably 100 to 500 per second) taken during that time period or step, and comparing the new average value to the immediately preceding average value determination, or some other mathematical comparison to prior average value determination(s). If the change is more than a predetermined change value (for example, 5 inches of mercury), an extreme condition is detected and recorded, and the pump will be activated immediately. The predetermined change value can be altered via the graphic user interface to accommodate variations in the prosthetic or orthotic device and their respective components.

It is noted that several methods to determine when to operate the pump are contemplated as different methods could be used for different patient applications. According to one embodiment, the method for determining when to run the pump are based on certain mathematical calculations and further influenced by logical decisions. One or more of the following considerations/calculations may be used to determine operation of the pump: the speed of patient, the average vacuum level in the short term (last 2 steps), the average vacuum level in the long term (last 8 steps), trends from step to step, the shape of the vacuum signature (e.g., running is different from walking (for running the speed of signal is faster, the excursion or variation of signal is greater, and the shape of signal is more digital because there is no heel strike)), the ratio of the variation levels of the vacuum signature, the rate of change of the running average, the location of the average level within the vacuum window, which is between the initiation threshold and the maximum vacuum setting (the priority or weight of the preceding components in the calculation may change depending where the signal is within the window).

For further explanation, for the automatic detection of the change from a faster pace to a slower pace, if the average vacuum or some other calculation of the vacuum is determined to be higher than needed, the controller may operate the solenoid valve 512 and reduce the vacuum to a comfortable level. For the automatic detection of a sitting or otherwise static condition, if the controller determines that the patient is static, one option would allow the system to reduce the vacuum by a predetermined amount to be more comfortable. For an automatic detection of a static to a dynamic condition when the system detects that the patient is now dynamic, the controller can operate the pump 502 to increase the vacuum back to a level that is appropriate for the activity level.

For example, the patient's normal vacuum setting is 15 inches of mercury. If the patient is sitting for a period of time and the controller detects this action, the vacuum may be reduced to 12 inches of mercury. If the patient stands up and starts walking, the system detects this change and immediately operates the pump 52 to restore the vacuum to the 15 inches of mercury. Furthermore, the controller may provide automatic detection of patient speed or position change and the associated actions, for example, automatic detection of the change from walking to jogging. If variations due to extreme pressure such as jogging are detected, the system can automatically activate the pump to increase the overall vacuum level to make the socket feel tighter and handle the stresses of running. FIG. 6(*e*) shows a vacuum signature (i.e., a series of sequential data points indicating the vacuum of the socket as a function of time) when jogging occurs.

The microprocessor 402 also can be used to compare a vacuum pattern with a learned patient pattern, anticipate a vacuum loss, and correct the vacuum before the initiation threshold is reached. As the wearer is in a dynamic mode (e.g., walking), the vacuum level will fluctuate as the patient applies and removes pressure during a step. This dynamic signal can be sampled at a rate that would provide a profile of the dynamic event. This could be thought of as somewhat similar to the immediately recognized signal provided by an ECG (ElectroCardioGraph) machine. Information in this pattern can be compared to previously stored patterns. If this pattern changes from the stored values, it could indicate a problem such as a loss of vacuum. For example, a normal vacuum pattern may have a fast negative rate of change at heel strike, then stabilize through the step, and then may have a fast positive rate of change at toe off. This cycle repeats every step. The total variation of the signal during this step may only be in the range of 0.5 to 1.0 inch of mercury. Initial testing of the patient can be used to determine a baseline from which all subsequent testing will be compared. If the rate of change of the signal changes significantly over time, or the variation values increase from the baseline values, it could be determined that the system is losing vacuum, or something is changing in the prosthesis that is affecting the fit and the vacuum levels. This condition would be recorded and the vacuum pump would be activated to restore the initial vacuum and fit. After the vacuum cycle reaches the maximum value the pattern or the fit should be the same or similar to the original fit. If it is not, this condition could also be recorded for future review. Some variation in the algorithm could be provided to allow for small weight changes or component wear.

The above-described processes could be used not only as an indicator of vacuum loss, but also could be a fit-change detector. The fit change could be caused, for example, by a failure or deterioration of system components, by patient weight gain/loss, or a loose/damaged foot or ankle. Anything that deviates from the initial fitting of the prosthesis would change the dynamic pattern of the vacuum signal.

Alternative to or in addition to the description above, other algorithms may be used to provide the requisite analysis, such as a moving average, comparisons with thresholds, pattern matching algorithms, gait analysis, or the like.

The microprocessor 402 also can be used to compare a vacuum pattern with a learned patient pattern to anticipate vacuum changes and control the vacuum pump in an economic and comfortable manner. For example, if the residual limb is a leg, while the patient is walking the microprocessor 402 can monitor the rate of change of the vacuum signals and can determine if the vacuum changes are due to the "pistoning effect" of the leg in the socket 102 or if the vacuum is actually leaking from the socket 120. Such monitoring can be used to determine when the vacuum pump should operate. If the vacuum is dropping to or beyond the initiation threshold and then returning to the valid range, the microprocessor 402 can determine whether this fluctuation is caused by normal walking movements. If so, the vacuum pump will not be operated if the vacuum returns to the valid range within an appropriate period of time. Because the patient's walking pattern can be recognized as cyclical and non-linear, control system will not cause the vacuum pump 502 to operate in short bursts on every step; thus increasing the system efficiency and battery life.

With the self-learning process described above, the initiation threshold for the vacuum can be set. The patient can be allowed to walk on the prosthesis in which a dynamic range could be determined and stored as that particular patient's reference maximum vacuum. In other words, the control structure could also operate without a maximum vacuum value set and then learn the patient vacuum pattern and set the correct value for the best socket suction and comfort for that patient. If the prosthesis is fit correctly and is comfortable to the patient, a learn mode could be activated, which would set the baseline for the dynamic vacuum pattern, the static vacuum pattern, the maximum vacuum, and the initiation threshold. Preliminary values for these variables would initially be used. These values could be determined by testing of many patients. For example, the starting maximum vacuum value could be 14 inches of mercury. The patient would walk for a period of time, five minutes for example. During that period the minimum and maximum vacuum values would be monitored. If the variation from maximum to initiation threshold exceeded a level of 3 inches of mercury, indicating a soft or spongy fit, the system would increase the maximum vacuum by 1 inch of mercury. This would continue until the patient vacuum values were within acceptable limits. The other parameters and the pattern would be set accordingly. Thus the system is adaptive to the changes in the socket vacuum values. This learning mode could be used exclusively by the medical practitioner or could be left on to be continuously adaptive.

The wireless transceiver 410 and the remote station 411 can be used to monitor the electronic and vacuum systems while the patient is walking to learn a myriad of parameters and operation conditions, which can be stored in the non-volatile memory of the microprocessor 402. The system log provides a valuable tool to allow the clinician to replay the chronology of events within the system. This information could be related to patient interaction, socket performance, maintenance or potential problems. For example, during operation of the control structure, the number of vacuum pump run cycles, the average vacuum pump run time, the number of times an initiation threshold is not being met, the number of charge cycles, the rate of vacuum changes, the dynamic variation in vacuum changes (i.e., the vacuum changes when the patient walking), and the static variation in vacuum changes (i.e., the vacuum changes when the patient sitting or resting) can all be monitored.

At least some of these parameters and operation conditions can be used to determine a Socket Quality Factor (SQF). The SQF is used to create an industry standard and set benchmarks for future socket designs by evaluating the fit and function of the socket and suspension compared to when it was initially dispensed. The data regarding the average number of times the pump activated per hour of wearing and the time it took for the pump to obtain maximum vacuum could be recorded and documented when the device is first fit. When the patient returns for follow up care, new data could be recorded and compared to the previous data to determine if the socket was still fitting within consistent parameters of the initial fitting and the clinician would have the information, data and insight to determine if adjustments to the socket and suspension were required. Additionally, when the socket is first fit, the operating parameters could be compared to an acceptable list. This could include, A) minimum vacuum to make the socket fit comfortably and feel securely connected. If the variation of the vacuum signal is large it could indicate a large void area in the socket which may feel spongy to the patient and may be easy to lose the vacuum sealing. If the variation of the vacuum signal is low it could indicate a socket that has a clogged vacuum path that could have been caused by trash left in the socket or tubing during socket fabrication, or is not installed correctly on the patient. B) A long pump run period along with a low vacuum level could indicate a leak in the system or a larger than normal void area in the socket. For example, the initial fitting could show a minimum vacuum level of 10 inches of mercury, a maximum vacuum level of 15 inches of mercury (absolute) and a pump time from 0 to minimum vacuum of 8 seconds and a minimum vacuum to maximum vacuum of 14 seconds. As the patient starts walking there will be dynamic components that can be recorded, such as a 2 inches of mercury change. The goal of this is to help troubleshoot the socket fitting and to establish a profile of what is a good fit compared to a poor fit. All socket variables and parameters could be formulated to create this SQF.

Additionally, at least some of the parameters and operation conditions can be used to obtain information about the quality of the control structure, the fit of the leg within the socket 102, and the amount of movement within the socket 102. For example, a socket 102 that requires a pump run time of only a short period of time (such as five seconds or less) to go from the initiation threshold to the maximum desired vacuum level would indicate a close fit between the inner liner 160 and the outer casing 158, having very little air to evacuate. Conversely, a socket 102 that requires a relatively long period of time (such as 45 seconds or longer) to evacuate would indicate that there is a large void area 156 between the inner liner 160 and the outer casing 158. While the vacuum system may reach the maximum desired vacuum level in this situation, the vacuum in the socket 102 would have large variations and would feel spongy to the patient. Also, in this situation, the socket 102 would probably be more likely to lose vacuum due to the poor fit. Thus, by monitoring the vacuum pressure of the vacuum system using the vacuum sensor 506, the quality of the fit can be determined by monitoring the vacuum fluctuations during the use of the control structure and the run time of the vacuum pump. For example, if during the initial fitting the pump activated and cycled an average of 4 times per hour and took 10 seconds to evacuate the air in the socket each activation, this would be identified and documented as the patient's baseline data. If on a 3 month follow up visit the pump was now activating and cycling an average of 8 times per hour and/or took 15 seconds to evacuate the air in the socket, it could be determined that there was a change in the condition of the prosthesis, and possibly a vacuum seal problem. A clinician would then be led to evaluate the seal of the socket, and look for changes in the patient's residual limb that could affect the fit of the socket and thus affect the efficiency and performance of the vacuum system.

As another example, vacuum value fluctuations are variations in the maximum to minimum vacuum levels. If a new socket only allowed 1 inch of mercury vacuum value change during walking, and three months later the same socket allows 3 inches of mercury vacuum value change during walking, a problem is indicated. This problem may not be caught by the pump run time because the difference in runtime to correct the problem may only be a minor amount, especially if the initiation threshold is not being achieved.

As another example, the number of vacuum pump run cycles can be used to identify the quality of fit or whether the socket or its components are faulty and/or leaking. A large number of vacuum pump run cycles may indicate a poor quality fit or that the socket components are faulty and/or leaking. A more moderate number of vacuum pump cycles may indicate a more appropriate fit that is not leaking. As indicated in the previous paragraph, an increased number of cycles will be a potential indicator of a change in the patient's condition, which would affect the fit of the socket and thus affect the efficiency and performance of the vacuum system.

As yet another example, the number of vacuum pump run cycles can be used to identify whether the patient is wearing the prosthetic device and/or using its control structure. A very small number of vacuum pump run cycles could indicate that the patient is not wearing the prosthesis or that the system is not in use, which would allow the medical practitioner to ask questions related to the socket or the systems of the control structure. For example, the medical practitioner may find that some of the reasons for non-use are related to the comfort of the fit, the pump runs too often so the patient turns it off, or the patient forgets to charge it at night, etc. The number of run cycles would be compared to the baseline data that was observed and documented during the initial fitting and dispensing of the device.

As yet another example, the average vacuum pump run time can be used to identify problems in the control structure. If the average vacuum pump run time is very low and the patient complains of spongy fit or no suction, there may be an obstruction in the vacuum line or a clogged vapor trap filter. The average pump run time would be compared to the baseline data that was observed and documented during the initial fitting and dispensing of the device.

As yet another example, the number of times an initiation threshold is not met can be used to identify additional problems. A very low value may indicate a problem with the donning of the prosthesis or that the components in the socket are not allowing the initial vacuum cycle to work correctly. This value would be determined during the initial fitting of the device and documented as the patient's baseline data.

As yet another example, the number of charge cycles can be used to determine whether the control structure is being properly charged by the patient. If the number of charge cycles is low when compared to the number of days worn, this may indicate whether the patient is charging the system daily or as required.

The procedures described in the preceding paragraphs indicate the calculated and automatic functions by the continuous monitoring of the system values and comparing them to known values and patterns. The system reacts to these events and records them. Information displayed for the clinician is real-time feedback, where the clinician could monitor the system and develop their own conclusions, or the clinician could review the system log to look for abnormalities or trends. However, the system status screen already contains the self diagnosis based on the problems encountered. In essence the system will diagnose the occurrences as they are logged and provide a determination of the system status. The clinician may then investigate the prosthesis and the system to look for errors.

As to providing feedback to the clinician, the controller of the prosthetic device may comprise a user interface to display the vacuum signature (sequential data points from the vacuum sensing mechanism or sensor over time) so that the clinician may analyze the sequential data points to determine a quality of fit between the receptacle and the limb of the patient by using the vacuum signature. The user interface may be graphically displayed. Through vacuum signature analysis, a visual presentation of realtime vacuum signature through a display allows the clinician to monitor the overall condition of the prosthesis and the physical alignment of the prosthetic components; thus, providing feedback that the clinician can interpret so as to create a prosthesis that fits comfortably and functions correctly. The vacuum signature may be displayed in real-time or a signature previously stored in a memory in the controller.

Figure 6A:
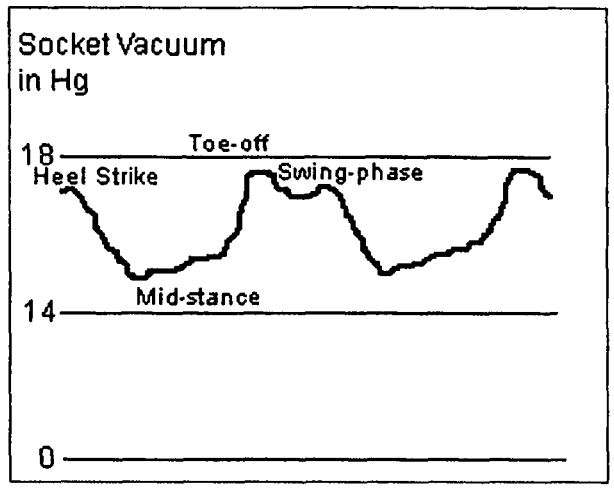
FIGS. 6(a) through 6(e) discloses vacuum signatures from sequential data points for a variety of conditions of wear according to an embodiment of the present invention.

FIGS. 6(a) through 6(e) discloses types of curves that may be shown to the medical practitioner or clinician under various circumstances. FIG. 6(a) shows a typical vacuum signature. The signature directly relates to each aspect of taking a step. The heel strike, mid-stance toe-off and swing phase are all clearly visible. The deviation in the vacuum signature is directly related to the pressures changing in the socket during the step.

Figure 6B:
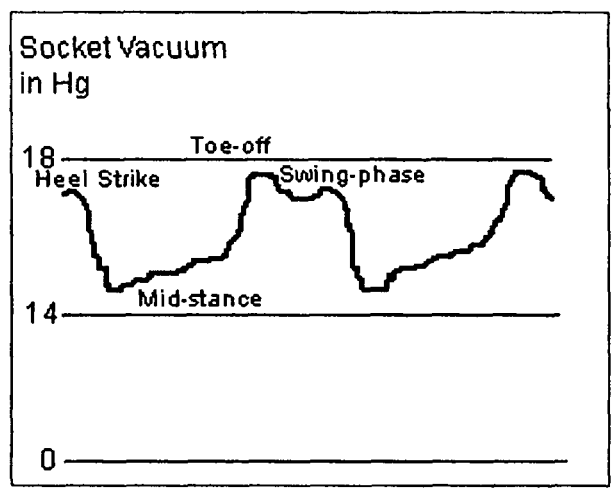

FIG. 6(b) shows a vacuum signature that has a pronounced heel strike. The slope of the signature indicates that most of the patient's weight and stress is being exerted immediately on heel strike. This stress could cause premature component failure of the prosthesis components as well as causing additional medical problems by transferring this pressure back to the patient through their residual limb. The near vertical line from swing phase to heel strike can be adjusted in the prosthesis to provide a smoother less stressful heel strike. Additionally, this vertical line could indicate that a different prosthetic component such as a different foot or ankle may be in order so as to reduce this stress. Heel strikes that are at excessive angles indicate significant stress being applied to the heel and ultimately back to the patient. Such heel strikes may indicate the need for an adjustment to lessen the heel strike stress or could indicate that another different foot, ankle or other prosthetic component may be required for this patient.

Figure 6C:
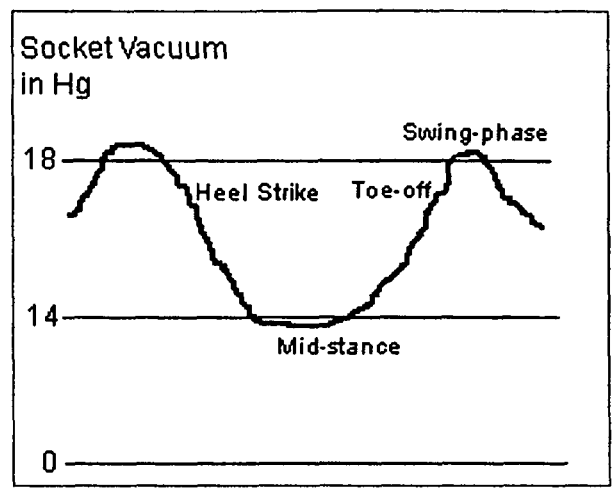

FIG. 6(c) shows a vacuum signature that has large variations (i.e., amplitudes) for the particular speed that the patient is walking. This form would indicate a loose-fitting socket or receptacle, which could be caused by a poorly fabricated socket, the patient lost weight or if the patient is wearing a sock that is too thin. For a tight feeling fit, there should be low vacuum variations. As can be seen in FIG. 6(c) the specific phases of the step are not pronounced; thus, the patient may complain that the leg is moving vertically, or feels soft or spongy.

Figure 6D:
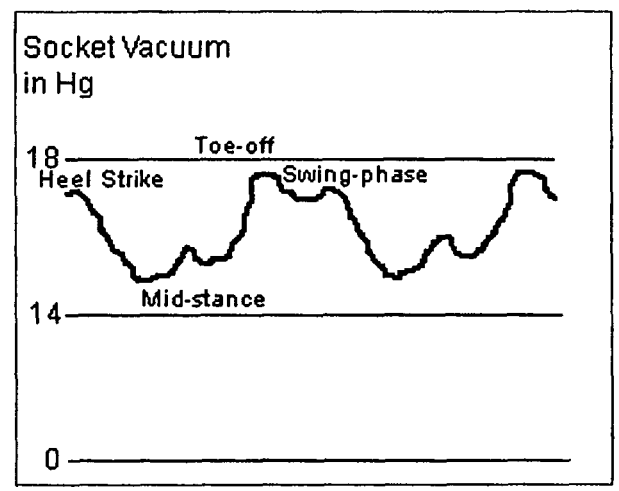
Figure 6E:
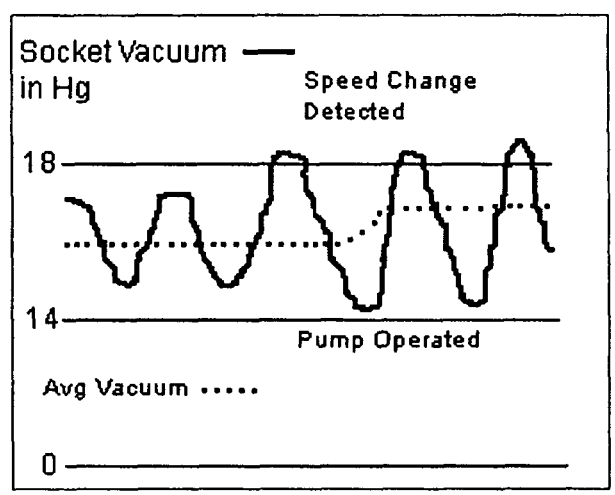

FIG. 6(d) shows an aberration 702 in an otherwise normal vacuum signature. Simple blips on the vacuum pattern could indicate an area that needs investigation. Using FIG. 6(d) as an example, the medical practitioner might see a subtle signal change during mid-stance. This positive-going signal indicates that some pressure is being removed then immediately returned to the normal level for that phase in the step. This reaction could be directly related to prosthesis alignment (a problem such as a loose bolt or binding) or could indicate some action that the patient is making that is unusual. For example, the patient may make this movement because something hurts and the patient is compensating for the pain, or maybe it is a learned motion that could be adjusted with therapy. In any case, the aberration indicates to the medical practitioner that something is happening at a certain time and requires investigation. With such a signature analysis, problems related the overall patient care could be detected, and not just the function of the components of the prosthesis.

To aid the clinician, templates may be created for various patient types and conditions to aid with the interpretation of the real-time data. Some examples include templates showing a vacuum signature with a certain artificial foot and ankle combination with a 2 ply sock on a 200 pound patient, the same artificial foot and ankle combination with a 5 ply sock on a 200 pound patient (because a 5 ply sock will have a different signature from a 2 ply sock), a vacuum signature with a different artificial foot and ankle combination with a shock absorbing pylon and a 5 ply sock on a 300 pound patient, and other similar kinds of templates.

The user interface may include a display, which can be presented to and manipulated by the medical practitioner. For example, the data may be in real-time continuous data or stored data. The display of the data may be started, stopped, scrolled forwards, scrolled in reverse, expanded, contracted, or the like.

Additionally this system allows for monitoring and recording the number of steps of the leg, the average speed of walking, the maximum speed of walking achieved, the speed of walking when a complete loss of vacuum occurred, the longest period of walking, etc.

A mode can be provided that will disable all of the automatic functions and make a SQF determination. This could be done at the initial fitting and anytime after that. For example, measurements could be taken while the patient is instructed to walk until the audible annunciator beeps, then sit down until the annunciator beeps again, and then walk again until the annunciator beeps yet again. During this test the static variations in the vacuum levels, the pattern of vacuum during dynamic conditions, and the variations of the dynamic vacuum levels could be determined. A baseline of acceptable performance will be created that assigns weights to these variables and a SQF will be determined. The actual values used to determine the SQF will be displayed to indicate what factors, if any, are causing the SQF to be outside of acceptable limits.

For example, the variation of the vacuum signature of FIG. 6(c) indicates the actual vacuum changing in the socket. For a tight feeling fit, this value should be low. A 5 ply sock will have a different signature than a 2 ply sock. Such a comparison can be performed using a pattern matching algorithm. If the SQF is outside acceptable limits, an annunciator can be activated.

A blip on the vacuum signature during the mid stance phase, such as that in FIG. 5, could also indicate that the foot has a problem like a loose bolt, or is binding. Such a comparison can be performed using a pattern matching algorithm. If the SQF is outside acceptable limits, an annunciator can be activated.

The system also could automatically read the system log (including date and time stamps) and determine conditions that should be addressed. For example, an algorithm in the program could look at the frequency of battery recharge cycles. If it is determined that the system is occasionally being charged every four days, this would indicate that the patient is not using the system properly and there are periods where the system is shut down and not being used. This determination could be displayed in a concise format such as "System is not being consistently recharged". This could be a patient related problem or could be an intermittent problem with the external power supply. Various other algorithms could additionally be used to give the clinician an immediate usage status. This automatic usage status feature could provide an immediate indication of an existing or potential problem and could alert the clinician to investigate and correct a situation that otherwise may be overlooked.

The above disclosure describes a control structure and method of operation that can be small, quiet, and reliable so as to ensure a consistent vacuum for the prosthesis connected to the patient. The versatility of the control structure can enable a medical practitioner to "retro fit" an existing prosthetic device with the control structure according to the present disclosure. In addition, the mechanical connections for the control structure can be easy to apply utilizing equipment and technology available in the clinical setting.

The control structure and its method of operation can be very intuitive to use such that a medical practitioner can be able to apply the technology with ease. Also, the interface of the remote station can permit easy adjustment of the control structure's operational parameters system.

The housing of the control structure is designed to wrap around the prosthetic pylon so as to reduce bulk and to be fitted under a cosmetic cover to enable a natural cosmetic finish to the prosthesis. The housing can be connected with a remote cable to enable the patient to connect the power supply to the housing for recharging the batteries. The housing can also be installed with a remote cable connected so as to enable the patient to turn remotely control the ON/OFF switch.

In addition, adjusting and monitoring the control structure can be accomplished by a laptop computer, hand held PDA, or other remote stations. Utilizing Bluetooth® technology or other telemetric and electromagnetic radiation communication, the medical practitioner can be able to monitor the specific maximum desired vacuum level within the socket in real time as the patient ambulates on the prosthesis and be able to adjust both the maximum vacuum draw available within the system as well as adjust the vacuum "initiation threshold."

The prosthetic device and control structure according to an embodiment of the present invention can be configured to be lightweight and miniaturized, while enabling a source of a substantially constant vacuum for connecting the prosthetic device to the residual limb of a patient during ambulation, sitting, or standing. The vacuum does not need to be dependent on the movement of the person.

According to an embodiment of the present invention, the control structure comprises a microprocessor that controls a vacuum device used to pull air out of the socket of the prosthetic device to create a vacuum within the socket that holds the prosthetic device on the patient's residual limb. The control structure is miniaturized in design and shape. Also, the microprocessor can be used to adjust and set parameters of the control structure, as well as monitor and manage the functions and operations of the control structure.

According to an embodiment of the present invention, an external control, such as a laptop computer or a hand held personal digital assistant (PDA), can be used to adjust and/or monitor the control structure. For example, Bluetooth® or other wireless technology can be used to enable a clinician to monitor the specific maximum desired vacuum level within the socket in real time as the patient ambulates on the prosthesis, to adjust the vacuum initiation threshold, and/or to adjust the maximum vacuum level available within the system.

Although the above disclosure has been describing the use of the invention in relation to connecting a prosthesis to a residual limb, other application are contemplated within the spirit of the present invention. For example, the control structure can be used to connect medical monitoring or diagnostic devices to various parts of the body including appendages.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention.

What is claimed is:

1. A prosthetic device comprising:
a connecting portion for connecting to a person using vacuum;
a control structure for controlling an amount of vacuum used to connect the connecting portion to the person, the control structure includes a vacuum pump in fluid communication with the connecting portion for controlling the amount of vacuum, a vacuum sensing mechanism for measuring the amount of vacuum, a first-in first-out buffer memory that stores a set number of average vacuum values, and a controller configured to receive input from the vacuum sensing mechanism and to control the vacuum pump to control the amount of vacuum, the control structure stores a minimum value for activating the vacuum pump and a maximum value for deactivating the vacuum pump, the controller configured to determine a continuous rate of change of average vacuum values based on the set number of average vacuum values stored in the first-in first-out buffer memory and to activate the vacuum pump if the continuous rate of change of the average vacuum values exceeds a predetermined change value; and
a wireless transceiver for outputting data related to the vacuum for display at a user interface, wherein the user interface is remote from the prosthetic device and remote from the person;
wherein the controller is configured to allow the maximum value and the minimum value to be adjusted via the user interface in increments of no greater than 0.1 inches of mercury.

2. The prosthetic device of claim 1, wherein the connecting portion includes a receptacle for receiving a limb of a person.

3. The prosthetic device of claim 1, wherein the data related to the vacuum includes at least one of actual vacuum, run time of the vacuum pump, and initiations of the vacuum pump.

4. The prosthetic device of claim 1, wherein the control structure is configured to store the data related to the vacuum in memory for later outputting and display at the user interface.

5. The prosthetic device of claim 1, wherein the data related to the vacuum includes data indicating at least one of fit, function, and status of the prosthetic device.

6. The prosthetic device of claim 1, further comprising a barometric sensor that provides an indication of an ambient pressure outside of the prosthetic device such that the control structure can calibrate the vacuum sensing mechanism to provide the same amount of absolute vacuum differential at various barometric pressures and at different operating altitudes.

7. The prosthetic device of claim 1, wherein the control structure includes a learning mode that automatically adjusts the maximum value and the minimum value based on a monitored patient vacuum pattern during use of the prosthetic device by the person.

8. The prosthetic device of claim 1, wherein the controller is automatically switchable between a static mode corresponding to the person sitting or standing still and a dynamic mode corresponding to the person moving, wherein the controller.

9. The prosthetic device of claim 8, wherein the set number corresponds to a set number of time periods when the control structure is in the static mode.

10. The prosthetic device of claim 8, wherein the set number corresponds to a set number of steps taken by the person when the control structure is in the dynamic mode.

11. The prosthetic device of claim 8, wherein the predetermined change value is a first predetermined change value when the controller is in the static mode, and wherein the predetermined change value is a second predetermined change value when the controller is in the dynamic mode, the second predetermined change value is greater than the first predetermined change value.

12. The prosthetic device of claim 1, wherein the controller is configured to activate the vacuum pump upon determining that the set number of average vacuum values indicates an extreme rate of change of the amount of vacuum.

13. A prosthetic device comprising: a connecting portion for connecting to a person using vacuum; a control structure for controlling an amount of vacuum used to connect the connecting portion to the person, the control structure including a vacuum pump, a controller and a first-in first-out buffer memory that stores a set number of average vacuum values, the controller configured to determine a continuous rate of change of average vacuum values based on the set number of average vacuum values stored in the first-in first-out buffer memory and to activate the vacuum pump if the continuous rate of change of the average vacuum values exceeds a predetermined change value; a wireless transceiver connected to the control structure; and a remote device including a display for outputting data related to the vacuum and a user input such that the person can adjust a vacuum initiation threshold pressure and a maximum vacuum pressure during use of the prosthetic device in increments of no greater than 0.1 inches of mercury, wherein the remote device is remote from the prosthetic device and remote from the person, and wherein the remote device receives the data from the wireless transceiver.

* * * * *